United States Patent
Sandri et al.

(10) Patent No.: US 11,628,602 B2
(45) Date of Patent: Apr. 18, 2023

(54) FILTER FOR THE EXCHANGE OF HEAT AND MOISTURE FOR APPLICATION IN THE MEDICAL FIELD AND PROCEDURE FOR THE PRODUCTION THEREOF

(71) Applicant: Consiglio Nazionale Delle Ricerche, Rome (IT)

(72) Inventors: Monica Sandri, Faenza (IT); Anna Tampieri, Faenza (IT); Simone Sprio, Bologna (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 748 days.

(21) Appl. No.: 16/489,504

(22) PCT Filed: Feb. 27, 2018

(86) PCT No.: PCT/IB2018/051234
§ 371 (c)(1),
(2) Date: Aug. 28, 2019

(87) PCT Pub. No.: WO2018/158684
PCT Pub. Date: Sep. 7, 2018

(65) Prior Publication Data
US 2020/0030566 A1 Jan. 30, 2020

(30) Foreign Application Priority Data
Feb. 28, 2017 (IT) .......................... 102017000022625

(51) Int. Cl.
*B29C 35/16* (2006.01)
*A61M 16/10* (2006.01)
*C08J 3/075* (2006.01)

(52) U.S. Cl.
CPC .......... *B29C 35/16* (2013.01); *A61M 16/1045* (2013.01); *C08J 3/075* (2013.01); *C08J 2305/08* (2013.01); *C08J 2489/06* (2013.01)

(58) Field of Classification Search
CPC ...... B29C 35/16; A61M 16/1045; C08J 3/075; C08J 2305/08; C08J 2489/06
USPC ........................................................ 264/28
See application file for complete search history.

(56) References Cited

U.S. PATENT DOCUMENTS

| 2012/0149111 A1* | 6/2012 | Wegst | .................. | C12N 5/0619 |
| | | | | 435/395 |
| 2013/0129634 A1* | 5/2013 | Tampieri | .................. | C01B 25/32 |
| | | | | 424/400 |

FOREIGN PATENT DOCUMENTS

| CN | 101703806 A | 5/2010 |
| CN | 103525097 A | 1/2014 |
| CN | 103724657 A | 4/2014 |
| CN | 105920679 A | 9/2016 |

OTHER PUBLICATIONS

A Guide to Freeze Drying for the Laboratory, LABCONCO, 12 pages, 2004 (Year: 2004).*
Cui et al. Fabrication of interpenetrating polymer network chitosan/gelatin porous materials and study on dye adsorption properties. Carbohydrate Polymers 132 (2015) 330-337. (Year: 2015).*
Effendi et al. Comparison on mechanical properties of single layered and bilayered chitosan-gelatin coated porous hydroxyapatite scaffold prepared through freeze drying method. IOP Conf. Series: Materials Science and Engineering 172 (2017) 012031 doi: 10.1088/1757-899X/172/1/012031. (Year: 2017).*
International Search Report and Written Opinion for corresponding Application No. PCT/IB2018/051234 (mailed Jul. 12, 2018).
Vazquez et al., "Natural Polymers as Heat and Moisture Exchange Devices for Medical Applications," Adv. Sci. Technol. 96:39-44 (2014).
Nguyen et al., "Preparation of Chitosan Coated Magnetic Hydroxyapatite Nanoparticles and Application for Adsorption of Reactive Blue 19 and $Ni^{2+}$ Ions," Sci. World J. 2014:1-9 (2014).
Panseri et al., "Iintrinsically Superparamagnetic Fe-hydroxyapatite Nanoparticles Positively Influence Osteoblast-Like Cell Behaviour," J. Nanobiotechnol. 10(32):1-10 (2012).

\* cited by examiner

*Primary Examiner* — Yih-Horng Shiao
(74) *Attorney, Agent, or Firm* — Troutman Pepper Hamilton Sanders LLP (Rochester)

(57) ABSTRACT

Filter made entirely with natural and biodegradable materials, for the protection of the respiratory tract of patients in the medical-surgical field and process for making it. The filter has a porosity or 80-98% and pore diameters of 100-350 micrometers and the pores have a shape of channels open at the ends, which are parallel to each other. The filter is obtained by preparing an aqueous solution of chitosan and an aqueous solution of gelatin, mixing them, pouring it into a container, keeping the container closed until obtaining a hydrogel and freeze-drying. A cross-linking step takes place by (a) adding a chemical cross-linker to the mixture of the chitosan and gelatine solutions and cross-linking before freeze-drying, or (b) subjecting the freeze-drying product to a thermal dehydration treatment.

8 Claims, 4 Drawing Sheets

FILTER FOR THE EXCHANGE OF HEAT AND MOISTURE FOR APPLICATION IN THE MEDICAL FIELD AND PROCEDURE FOR THE PRODUCTION THEREOF

This application is a national stage application under 35 U.S.C. § 371 of PCT Application No. PCT/PCT2018/051234, filed Feb. 27, 2018, which claims the priority benefit of Italy Patent Application No. 102017000022625, filed Feb. 28, 2017.

FIELD OF INVENTION

The present invention refers to a filter, made entirely with natural and biodegradable materials, for the protection of the respiratory tract of patients in the medical-surgical field; the invention also refers to the process for making the filter.

BACKGROUND

In healthy subjects, breathing normally occurs through the upper airways, that is essentially the nose, pharynx and larynx. In passing through these parts, the inspired air is heated and humidified; furthermore, the mucus of which the internal surfaces of these parts are coated, have bacteriostatic ability and of capture of particles suspended in the air. The air inhaled through these routes thus reaches the lungs in optimal conditions for their correct functioning.

In the course of surgical interventions or in chronic pathological situations, however, the upper airway are bypassed. In the course of surgical interventions under total anesthesia, the patient is intubated and breathing is forced through ventilation systems with ducts that bring the entry point of air into the body directly at trachea level; forced ventilation can also be prolonged in the case of bedridden patients with breathing difficulties; the entry of air from the trachea also occurs in the case of tracheostomised patients.

In all these cases, the patient is at risk of pulmonary complications, due to the fact that the inhaled air has too low temperature and humidity, or because of the entry directly into the lungs of germs, pathogenic substances or particulate matter.

To overcome these problems, filters capable to exchange heat and humidity with the surrounding environment are employed; these filters are known in the art with the abbreviation HME (Heat and Moisture Exchange), which will be used in the rest of the present description.

In principle, the operation of HME filters is based primarily on their ability to absorb heat and moisture from the air exhaled by the patient and release them to the incoming air during inspiration, and secondly on the ability to retain dust and pathogens (at least those of greater dimensions), thanks to the reduced dimensions of their porosity.

In the practical realization of these filters, however, difficulties are encountered.

U.S. Pat. No. 5,035,236 describes an HME filter in which the filtering element consists of a glass fiber membrane soaked in silicon oil; filters of this type are very cumbersome, and the filtering and heat exchange surface is very small compared to the overall size of the filter. These filters also present the problem of a relatively high pressure drop across the two faces of the membrane, which makes patient breathing difficult; to overcome the problem, the membrane surface must be increased, but this further increases the size and weight of the filter.

More common are the filters made with synthetic polymer foams with open porosity, typically polyurethane foams. The polymer foams, however, have the characteristics of being generally non-hygroscopic, so that they do not effectively absorb moisture from the vapors and gases exhaled by the patient; moreover, their thermal exchange properties are also not optimal. To solve these drawbacks, these foams are loaded with substances having suitable properties, such as hygroscopic salts to improve the moisture exchange, activated carbon or molecular sieves (U.S. Pat. No. 4,619,948) to improve the retention capability of harmful species, or aluminum powder (WO 94/01489 A1) to improve the thermal exchange properties of the filters. However, these solutions require elaborate production procedures, and each of them solve only one of the aforementioned drawbacks: for example, activated carbons and molecular sieves improve the performance from the point of view of the retention of harmful species but not the characteristics of heat exchange, while metal powders are only effective for improving these latter.

Porous materials obtained from the chitosan cross-linking with a gelatin, for use in general in the medical field, are known from various Chinese patent applications.

Application CN 103525097 A describes the production of spongy materials based on fish skin gelatin, alone or in a mixture with chitosan, starting from aqueous solutions containing acetic acid and optionally glutaraldehyde as cross-linker; after drying of the polymeric network by freeze-drying, products are obtained which are said to have a uniform microstructure of the pores and good moisture absorption properties, and which are indicated as generally useful in the biomedical field.

Application CN 105920679 A is directed to the preparation of a porous material useful for the regrowth of the skin. This material is obtained by cross-linking and extraction of the solvent by freeze-drying from solutions containing a gelatin and chitosan in ratios between 0.5:1 and 1:1; in particular, in view of the required application, the drying by freeze-drying is carried out in order to have porosities with a gradient of diameter, which is between 5 and 70 µm at a face of the manufactured article, and between 50 and 200 µm on the opposite side.

Application CN 103724657 A describes the production of porous materials to be used as scaffolds for the re-growth of tissues in general; the main components are gelatin and chitosan, which are reticulated with the use of an organosilanic compound. The structure of the material has porosity of large dimensions, between 100 and 300 µm, inside which porosities of smaller dimensions are contained; this particular porosity hierarchy is said to be useful for promoting cell proliferation.

Application CN 101703806 A describes porous composite materials with three components, hydroxyapatite (particles of 2-20 µm in size), chitosan and gelatin, in weight ratios of 3:3:4. These composites have porosity dimensions even higher than those of the material of the previous application, in the order of 300-400 µm.

Finally, the article "Natural polymers as Heat and Moisture Exchange devices for medical applications", B. Vazquez et al, Advances in Science and Technology, vol. 96, 2014, pages 39-44, describes a new type of HME filter made with a natural polymer, chitosan, functionalized with gelatin.

For use as an HME filter, a porous material must have a well balanced set of properties. From the chemical point of view, it must first have good moisture exchange properties (absorption from moist air and release in dry air or with a low moisture content); the cross-linking process carried out on the device must be such as to guarantee an adequate chemical stability and mechanical resistance of the material to the gas passage, properties that must be preserved even in humid conditions so as to avoid the collapse of the structure due to the pressure exerted by the passing gas. Moreover, from the structure point of view, it must have pores of sufficiently small size to retain dust and pathogens, but not such as to generate a difficulty in the air passage and therefore an excessive pressure drop, which would make it difficult to breathe to patients already debilitated in this function; and finally, it must naturally have porosity oriented in the sense in which the material must be traversed by the air.

The porous materials of the prior art do not have all together these characteristics, because the sponges of CN 103525097 A have uniform porosity and without a preferential orientation; the material of CN 105920679 A presents porosity of less than 70 μm on a face of the manufactured article, such as to generate an excessive obstacle to the air passage; also the porosity structure of CN 103724657 A, with porosity of large dimensions containing porosity of smaller dimensions, can give rise to excessive pressure drops at the two ends of the filter; the materials of CN 101703806 A have, instead, porosity of excessive dimensions, such as not to effectively retain particulate matter, germs and bacteria; and the aforementioned article by B. Vazquez et al reports only very general and incomplete information on the composition, the type of cross-linker used, the preparation method and the freeze-drying conditions of the studied HME filters, and does not give indications if these filters do or do not show a preferential direction of porosity, parameter of fundamental importance to guarantee a correct and prolonged operation of the device.

The aim of the present invention is to provide a new filter for HME application which overcomes the problems of the prior art.

SUMMARY OF THE INVENTION

This purpose is achieved with the present invention, which in a first aspect relates to a process for the production of a material useful for the production of HME filters; in a second aspect thereof, the invention relates to the material obtained with said process and the HME filters produced with this material; finally, in a third aspect, the invention relates to an HME filter with a composite structure, which favors the control of the temperature of the filter itself and therefore of its characteristics of pre-heating of the inspired air and of release of moisture thereto.

Figure 1C:
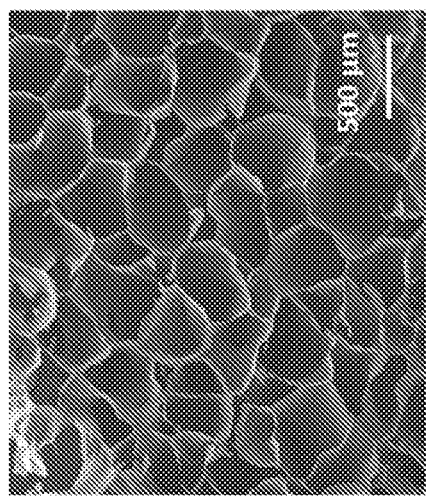
FIG. 1a shows a photograph of the material of the invention.
Figure 1B:
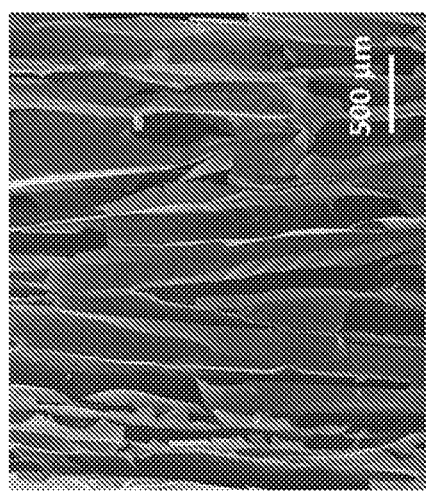
Figures 2A, 2B, 2C:
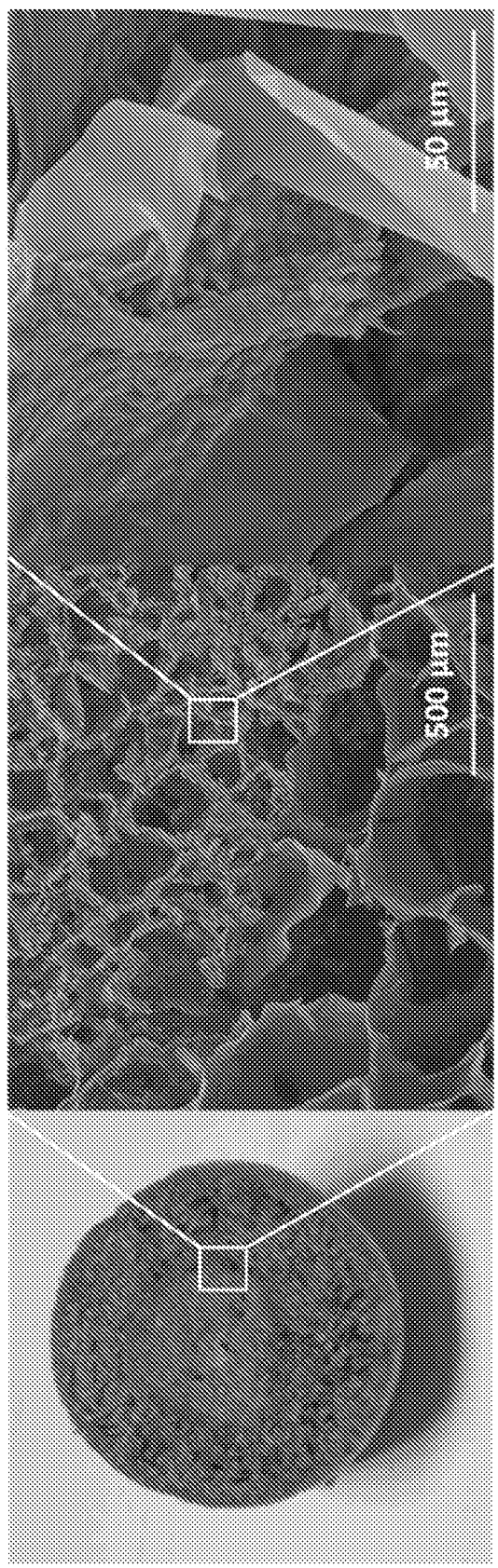
Figure 3:
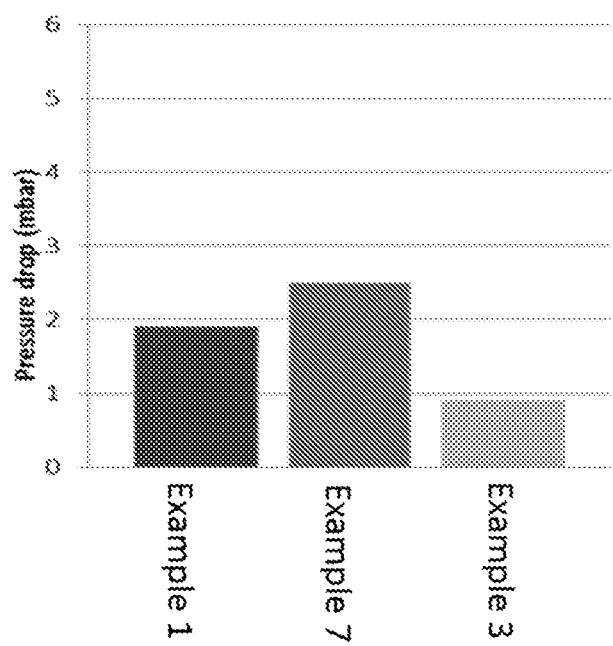
Figure 4:
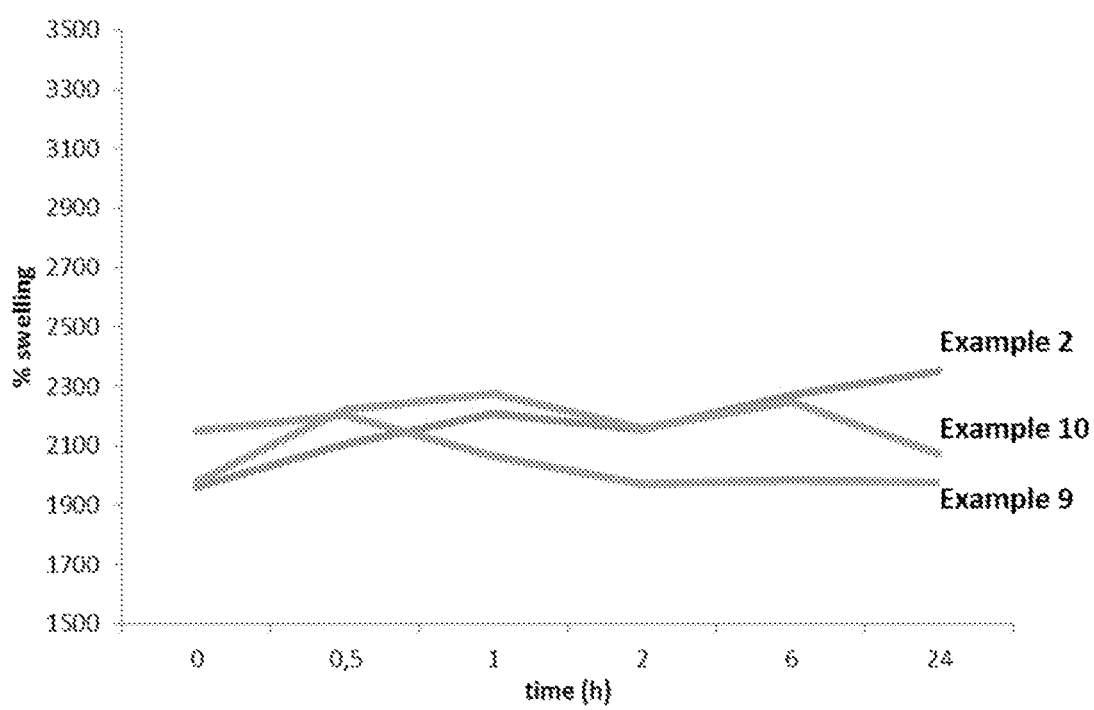
Figure 5:
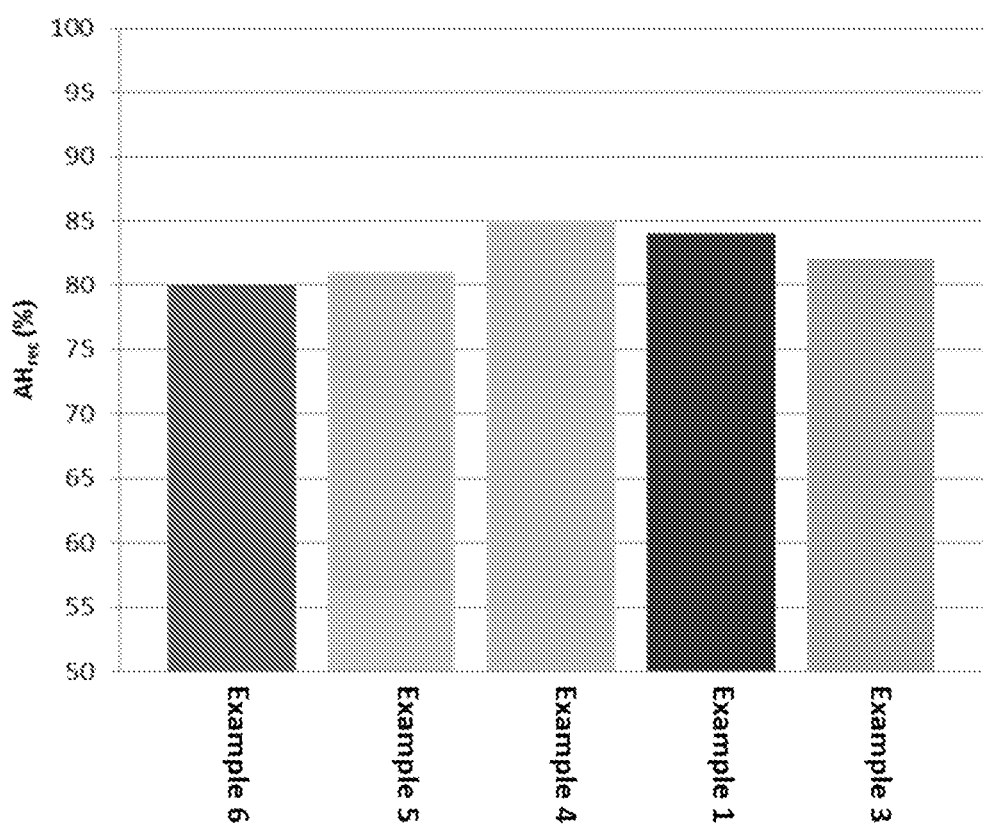

the FIG. 1b shows an electron microscope photograph of the material of the invention, in a longitudinal section thereof;

the FIG. 1c shows an electron microscope photograph of the material of the invention, in a transverse section thereof;

the FIG. 2a shows a photograph of a material of the invention according to the third aspect thereof;

the FIG. 2b shows an electron microscope photograph of the area at the edge between the filter material and the internal heating magnetic material;

the FIG. 2c shows an electron microscope photograph of the heating magnetic material of FIG. 2b;

the FIG. 3 represents in graph form the results of pressure drop tests at the ends of an air filtration device obtained with three samples of material made according to the invention;

the FIG. 4 represents in graphical form the results of water absorption tests on three samples of material made according to the invention; and the FIG. 5 represents in graphical form the results of moisture absorption tests by five samples of material made according to the invention.

DETAILED DESCRIPTION OF THE INVENTION

The invention is hereinafter described in detail with reference to the Figures.

In its first aspect, the invention relates to a process for the production of a material useful for the production of HME filters that comprises the following steps:

a) preparing an acidic chitosan solution at a concentration of 1 to 2.5% by weight;

b) preparing an aqueous solution of a gelatin of animal origin at a concentration from 2.5 to 5% by weight, operating at a temperature between 40 and 50° C.;

c) mixing the two solutions thus obtained in quantities such as to obtain a weight ratio gelatin:chitosan from 80:20 to 50:50, preferably 70:30, gently shake the resulting solution to avoid the formation of a foam until a homogeneous solution is obtained, and subsequently dilute the mixture to obtain a total polymer concentration of from 2 to 4%, preferably 2%, by weight;

c') optionally, adding a chemical crosslinker to the solution obtained in step c);

d) pouring the solution prepared in step c) or step c') into a container with the bottom made of a material having thermal conductivity greater than or equal to 15 W/(m·K) and side walls made of a material having thermal conductivity less than or equal to 1 W/(m·K);

d') if step c') has been carried out, keeping said container closed until obtaining a hydrogel;

e) freeze-drying, inside said container, the solution obtained in the step c) or the hydrogel obtained in step d') according to the following phases:

hydrogel freezing at a temperature between −20 and −60° C., preferably −40° C., made by contacting the bottom of the container with a refrigerating system;

primary drying by heating with a speed between 2 and 8° C./h up to a temperature between −5 and −10° C., operating at a pressure between 0.001 mbar and atmospheric pressure;

secondary drying by heating with a speed between 1 and 5° C./h up to a temperature between 15 and 20° C., operating at a pressure between 0.001 mbar and atmospheric pressure;

f) if the steps c') and d') have not been carried out, submit the freeze-dried product obtained in step e) to a cross-linking treatment by thermal dehydration.

The inventors discovered that a careful control of all the conditions of the process described above is of fundamental importance for obtaining HME filters. As mentioned in the introduction, an HME filter must have definite properties of heat and moisture exchange ability, as well as of retention of particles, germs and the like, characteristics that improve with the reduction in the size of the filter pores; at the same time, the filter must offer the minimum resistance possible to the patient inhalation effort, and therefore the minimum pressure drop, a feature that improves with increasing pore size. The process of the invention allows obtaining the set of these properties in ranges of acceptable values for use in HME filters.

In the following description, all quantitative ratios between components, all percentages and all concentrations of the solutions are by weight, unless otherwise indicated.

The process of the invention admits two variants, which have in common the steps from a) to c) and which differ from each other, in the subsequent steps, for the moment and the manner in which the cross-linking of the polymeric components (chitosan and gelatin) is carried out.

The first step of the invention process, a), consists in preparing an aqueous chitosan solution.

Chitosan is a naturally derived polymer commercially available from many suppliers, which is obtained by deacetylation (generally under basic conditions) of chitin, the material that forms the exoskeleton of insects, marine crustaceans and the like, but also a major component of the cell wall of mushrooms (such as basidiomycetes, ascomycetes, and ficomycetes). For the purposes of the invention, it is not necessary that the chitosan used be 100% deacetylated; the products available on the market have a degree of deacetylation between about 70-80%, more than sufficient to allow the solubilization of the polymer in slightly acidic solutions (pH 6).

For the preparation of the solution, chitosan is dissolved in an acidic solution, for example at a pH lower than 6; the solvent is preferably an aqueous solution at a concentration of 1% acetic acid, having a pH of about 5.5. Chitosan is used in such quantities to form a solution of concentration from 1% to 2.5%. In order to facilitate the chitosan dissolution it is preferable to subject the initial mixture to vigorous stirring, for example with the aid of an ultrasonic bath to facilitate the disintegration of the particles, for a time generally ranging from about 10 minutes to 1 hour.

To carry out the second process step, b), an animal gelatin is used. Gelatin is also used in such quantities as to form a solution having a concentration between 2.5% and 5%. The gelatin is dissolved in water, generally at a temperature between about 40 and 50° C. and under stirring; in these conditions, the dissolution takes about 1 hour.

As will be immediately clear, the two previous steps have been named a) and b) for clarity of exposure, but this does not imply any necessary time sequence in their realization, and step b) can be realized before, after or at the same time as a).

In step c) of the process, the two solutions prepared in the previous steps are mixed together. The volumes of the two solutions are chosen in such a way that the weight ratio between gelatin and chitosan is between 80:20 and 50:50, and preferably equal to 70:30. The solution immediately obtained from the union of the two previous ones must be stirred to favor their homogeneity; the stirring must however be bland, to prevent the formation of foam. The maximum stirring intensity of the mixture can be checked visually, verifying that in fact there is no foam formation; in the experience of the inventors, with solution volumes of about 700-800 mL, magnetic stirring was used in a useful way at speeds of up to 500 rpm.

To obtain a suitable material for the application as an HME filter, the chitosan and gelatin present in the solution obtained by step c) must be cross-linked to consolidate the structure giving it both chemical and structural stability that is preserved even in wet conditions in which the device operates, in addition to regulating the degree of *hydrophilia* of the material being formed; moreover, it is necessary to dry the obtained material.

After the completion of the step c), the process can follow two alternative embodiments, which differ from each other due to the fact that in the first one the solution obtained in the step c) is first subjected to the crosslinking treatment between chitosan and gelatin, obtaining a hydrogel which is subsequently dried by freeze-drying, while in the second one the order of these two passages is inverted, the solution is first freeze-dried and then reticulated by a heat treatment.

The first variant of the process is completed with the steps from c') to e).

In this embodiment, crosslinking is done by chemical means. To the solution obtained in the step c), a compound capable of forming bonds both with chitosan and gelatin, forming "bridges" between the two materials, is added with step c'). Suitable compounds for this purpose are 1,4-butanediol diglycidyl ether (known in the art as BDDGE), glutaraldehyde, tannic acid and, preferred, genipin, a chemical compound extracted from the *gardenia* fruit; all these compounds are of common commercial availability and are also safe for the present application, finding wide use in the production of biomedical devices and in the food industry. The crosslinking compound is added in amounts ranging from 0.5% to 4%, preferably 1%, with respect to the sum of the chitosan and gelatin weights, preferably in the form of an aqueous solution thereof (all the mentioned compounds are soluble in water).

The solution obtained in step c') is poured into the container of step d), inside which the crosslinking reaction (step d') takes place at room temperature (20-25° C.); the product of step d') is a hydrogel. During all the time required for cross-linking, the container is kept closed to avoid water evaporation, phenomenon that could influence the hydrogel concentration and the structure of the material being formed. Crosslinking is generally complete in a period of 1-3 days, and in the case of genipin it can be monitored by the change in color, which changes from the light yellow of the starting solution to the dark blue-green of the final hydrogel.

The container has a thermally conductive bottom and thermally insulating walls, so as to allow a correct cooling/freezing profile of the hydrogel during the subsequent freeze-drying phase; more precisely, as mentioned, the container bottom must have a thermal conductivity equal to or greater than 15 W/(m·K), while the walls must have a thermal conductivity equal to or less than 1 W/(m·K). As examples of suitable materials, the bottom of the container can be made of steel, copper or silicon, while the walls can be made of materials of various types, such as plastics (eg, PVC or polyethylene), teflon or glass.

Finally, in step e), the hydrogel obtained in step d') is dehydrated by freeze-drying. The freeze-drying process is carried out at a pressure between 0.001 mbar and atmospheric pressure, and consists of a first freezing step of the hydrogel at a temperature from −20 to −60° C., preferably −40° C., followed by a primary drying by heating with a speed between 2 and 8° C./h up to a temperature between −5 and −10° C., and finally a secondary drying by heating with a speed between 1 and 5° C./h up to a temperature between 15 and 20° C. In particular, the above-described cooling and freezing phase is carried out by placing the bottom of the container in contact with the refrigerating system so that the cold transfer takes place in a completely directional manner from the bottom to the top; this operating mode, combined with the different thermal conductivity of the bottom and the walls of the container described above, allows to obtain porosities in their turn directional, with channels completely open and aligned in the vertical direction. Operating with the directional, and in particular vertical, heat transfer mode, is not strictly necessary for the subsequent heating phases; however, for convenience these subsequent phases can be realized in turn by heating the bottom of the container, so to realize the whole process in the same container.

In the second variant of the process, steps c') and d') are not carried out, and the process is completed with step f).

Steps d) and e) are carried out in a manner identical to that described for the first variant of the process, except in this case, in step d), the solution which is poured into the container does not contain a chemical crosslinker.

In this variant cross-linking is carried out, in step f), with a thermal dehydration treatment, which consists in subjecting the already freeze-dried material to a temperature ranging from 140 to 160° C., preferably 160° C., at a pressure between 0.001 mbar and atmospheric pressure and for a duration between 24 and 48 h. Despite not having carried out targeted research, based on what is reported in literature, the inventors believe that crosslinking takes place through condensation reactions (i.e., by water elimination) among functional groups present on the different organic materials, for example between the amino groups of chitosan and acid groups of gelatin (amidation reactions).

In both process variants, the final product has the consistency of a fairly rigid sponge, and can undergo mechanical processing not too intense, for example directed to remove, with a slicer or a scalpel, the surfaces above and below the material that may have too small pores; preferably, however, the material obtained after freeze-drying is not mechanically worked, so that the container in which the gel is formed has the geometry and dimensions of the final porous body to be obtained.

In its second aspect, the invention relates to the material obtained with the process described up to now. The material has a mixed gelatin/chitosan composition, in which the two components are present in the weight ratio determined during the production process by the ratio between the volumes of the corresponding solutions used in step c). The material obtained according to the process described above has a porous structure, with a porosity degree (ratio between the volume of the pores and the apparent volume of the material) ranging from about 80 to 98% and pores with a diameter between 100 and 350 µm.

The material porosities have the characteristic of having a strong anisotropy in their form, presenting as open channels at their ends, then on the opposite faces of the filter, and essentially parallel to each other. The direction of the channels, hereinafter referred to as longitudinal direction, is that determined by the temperature gradient that occurs during the freeze-drying phase, step e) of the process above described; this direction is therefore parallel to the vertical direction during the freeze-drying of the material. The direction orthogonal to the longitudinal one is called transverse.

Figure 1A:
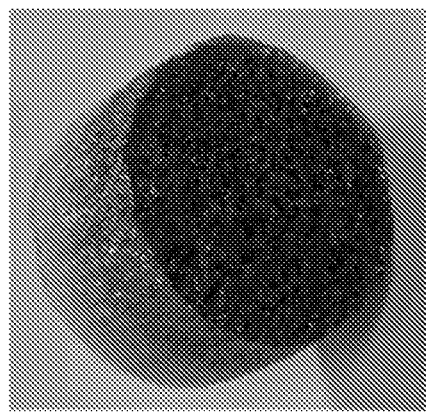

FIGS. 1a, 1b and 1c show, respectively, a photograph of a filter obtained with the invention process, and two photographs at 50× magnification obtained with a scanning electron microscope (SEM) on a section of said filter along the longitudinal direction of the material, and on a filter section along the transverse direction.

In an alternative embodiment, which constitutes a further aspect of the invention, the gelatin/chitosan material is produced around a "core" of a different material, having paramagnetic properties.

The "core" consists of a composite material, formed by a hydrophilic polymer mineralized and/or mixed with magnetic particles such as iron oxides (magnetite, maghemite, . . . ) or a hydroxyapatite modified with the addition of iron.

Hydroxyapatite is the compound of formula $Ca_5(PO_4)_3(OH)$, which exists in nature as a mineral and is also the mineral constituent of human and animal bones. The compound is also indicated in the literature also with the abbreviation HA. The compound offers many possibilities of modification through partial replacement of the component elements; for example, in the natural mineral the hydroxyl ion can be partially replaced by chlorine, fluorine or carbonate ions. For the present invention purposes, an amount ranging from 2 to 40% atomic of calcium is substituted by iron present in both its valences (II) and (III), which confers paramagnetic properties to the compound.

The hydrophilic polymer used for the mineralization with hydroxyapatite is preferably an alginate, in particular sodium alginate, but the invention can also be carried out with other hydrophilic polymers, such as gelatin, nanocellulose, chitosan or their mixtures. In the following the paramagnetic "core" production is described by referring, for brevity, to sodium alginate, but it is understood that this material can be replaced with any hydrophilic polymer, preferably of a natural type.

In its first aspect, the paramagnetic "core" useful for the invention is produced by a so-called "biomineralization" process, in which the modified HA (hereinafter referred to as FeHA) is formed, in the form of nanoparticles of size generally not higher than 200 nm, directly inside the sodium alginate matrix.

The process for the realization of the "core" includes the steps of:

g) preparing an aqueous solution containing a calcium precursor, at least one soluble iron (II) salt and at least one soluble iron (III) salt;

h) preparing an aqueous solution containing a water-soluble phosphorus compound, preferably phosphoric acid;

i) preparing an aqueous solution containing a precursor of one or more hydrophilic polymers;

j) slowly adding the phosphorus compound solution to the solution containing the calcium precursor and the iron salts, obtaining a suspension;

k) optionally, immediately adding the solution obtained in step i) to the suspension obtained in step j);

l) if step k) has been carried out, allow the system to react at a temperature between room temperature and 70° C. for a time between 1 and 5 hours;

k') in the event that the k) and l) steps have not been carried out, allow the system obtained in step j) to react at a temperature between room temperature and 70° C. for a period between 1 and 24 hours; and l') if step k') has been carried out, mix the obtained suspension with the aqueous solution obtained in step i);

m) subjecting the product obtained in step l) or step l') to a freeze-drying treatment;

n) immersing the freeze-dried product in a solution of $CaCl_2$ at a concentration between 0.5 and 1.5 M for a period of time between 15 and 45 minutes, at the end of which washing the device by immersion in distilled water;

o) subjecting again the material to a freeze-drying treatment.

Steps g), h) and i) can be performed in any order or at the same time. The amounts of reagents are calculated so that the weight ratio between modified HA and sodium alginate in the final product is between 40:60 and 60:40. The freeze-drying process is preferably carried out inside a container having the shape and dimensions corresponding to those of the desired core, in such a way that the same is ready for use, without the need for mechanical processing, at the end of the described process.

The production process of the paramagnetic core can be carried out according to two alternative methods, which differ in the execution order of the intermediate steps between j) and m).

In the first embodiment, the core is produced by immediately mixing the hydrophilic polymer(s) solution of step i) with the HA precursors (steps k and l).

In the second embodiment, the paramagnetic core is produced by mixing said hydrophilic polymer(s) solution with modified magnetic HA (FeHA) or iron oxide nanoparticles previously produced. Operating according to this variant, the formation of a modified hydroxyapatite precipitate is first determined, and to the suspension of FeHA particles thus obtained is added the hydrophilic polymer(s) solution, so that said FeHA particles are incorporated into the matrix of said polymer that is formed in steps from m) to o).

The hydrophilic polymer of the step i) preferred for the purposes of the invention is sodium alginate.

The amounts of magnetic phase and polymer are calculated so that the weight ratio in the final product is between 40:60 and 80:20. The freeze-drying process is preferably carried out inside a container having the shape and dimensions corresponding to those of the desired core, so that the same is ready for use, without the need for mechanical processing, at the end of the described process.

The paramagnetic core thus produced is then placed in the bottom and in the center of the container in which the process described above is carried out, comprising the steps from a) to e) or f). The solution obtained in step c') (in the first variant of the process) or in step c) (in the second variant of the process) is added to the container, so as to surround the paramagnetic core, so that with cross-linking and subsequent steps of hydrogel formation and of freeze-drying the core is surrounded by and adheres to a "shell" of the gelatin/chitosan material.

The core has a porous structure, but with porosity dimensions significantly lower than those of the gelatin/chitosan shell, so that the gases pass preferably through the latter, which maintains its function of heat and moisture exchange with the gases and vapors with which it comes in contact. The paramagnetic core can be heated from the outside with an alternating magnetic field, controlling with precision its temperature, and consequently also that of the overall filter. The active heating of the filter improves the properties of the same in releasing the humidity to the inhaled air, as well as, of course, bringing the temperature of the same to values closer to the physiological ones and therefore more comfortable and above all that result in lower health risks of the patient.

The composite filter thus obtained is shown in FIGS. 2a, 2b and 2c.

FIG. 2a shows a photograph of the filter as a whole, in which the boundary zone between the HA/alginate core in the center and the gelatin/chitosan shell on the outside is evident.

FIG. 2b shows a photograph at a 100× magnification obtained with a SEM of the interface area between the core and the shell of FIG. 2a.

Finally, FIG. 2c shows a 1,000× magnification photograph obtained with a SEM of the core, from which the modified HA nanoparticles connected to the alginate structure are evident.

The HME filter of the invention offers various advantages with respect to analogous filters of the prior art.

In the first place, it is completely formed from natural materials derived from renewable sources, in particular from the recycling of waste from the food industry that are completely biodegradable and which can be produced by means of green production processes and therefore of virtually null environmental impact. Consequently these devices are of high industrial interest as a consequence of the low cost, of the complete biodegradability (both aspects of fundamental importance as they are not reusable devices, but disposable) and, not least, the possibility of adapting to the European Community directives aimed at stimulating the creation of spinnerets for the waste recycling for the protection of the environment and of human health.

Secondly, its components have natural antibacterial and antiviral properties, so that the filter acts to protect of the patient respiratory system not only in a passive way (physically retaining possible pathogenic elements), but also actively.

Finally, the described core/shell embodiment allows, at a low price, to add the temperature control functionality that allows to obtain further improved functional properties with respect to the commercially available HME filters.

The invention will be further described by the following experimental section, including the description of the methods for carrying out the characterization tests, and the examples of production of various forms of composite material of the invention and measurement of their properties.

Methods and Instrumentation

Morphological Analysis with ESEM

The samples morphology has been analyzed using an environmental scanning electron microscope (ESEM, Quanta 600 FEG, FEI Company, Hillsbrono, Oreg.). The samples were mounted on aluminum supports with carbon ribbon and subsequently made conductive by a thin and uniform gold coating deposited by means of a Polaron Sputter Coater (Mod. E5100, Polaron Equipment, Watford, Hertfordshire, U.K.)

Porosity Determination

The porosity of the filters has been evaluated by the apparent density method. The apparent density of the filter is initially calculated as the ratio between its weight and its geometric volume; in the most common case, in which the filter has a cylindrical shape, the apparent density is calculated by means of the equation:

$$\rho_{apparent} = \frac{W}{\pi \times \left(\frac{D}{2}\right)^2 \times H}$$

wherein:

$\rho_{apparent}$ is the apparent density;

W is the weight of the filter; and

D and H are the diameter and height of the filter, respectively.

Subsequently, the theoretical density is calculated considering the different theoretical densities of the materials that compose the sample and the different ratios by weight, as shown in the equation below where X is the fraction by weight of the sample components:

$$\rho_{theoretical} = (\rho_{theoretical(component\ A)} \times X_{component\ A}) + (\rho_{theoretical(component\ B)} \times X_{component\ B})$$

Finally, the relative density ($\rho_{relative}$) is calculated as the ratio between the apparent density and the calculated theoretical density.

$$\rho_{relative} = \frac{\rho_{apparent}}{\rho_{theoretical}}$$

From the knowledge of the relative density, the porosity is obtained as shown in the following equation:

porosity (%)=(1-$\rho_{relative}$)×100

Determination of the Ability to Absorb Water (Qs)

The ability to absorb a certain amount of water (also called swelling) has been evaluated by immersing the sample in an aqueous solution containing 0.1% (w/v) of sodium azide ($NaN_3$) at 37° C. At specific time intervals, the sample has been extracted from the solution, lightly buffed to remove the surface solution and weighed. Swelling is calculated with the following formula:

$$Qs = \frac{W_s - W_d}{W_d}$$

wherein $W_s$ is the weight at the specific time and $W_d$ is the initial weight of the dry sample.

Measurement of the Contact Angle

The affinity that the material has with water has been evaluated by measuring the static contact angle on materials in the film form. To produce non-porous films suitable for the measurement, the hydrogel has been distributed as a thin film on the surface of a microscope slide and air-dried at room temperature.

About 1 μl of distilled water was dropped onto the surface of the film and the static contact angle of the drop has been measured using the "Video-Based Optical Contact Angle Meter" tensiometer (OCA 15+, Innovent, Germany).

Evaluation of the Pressure Drop

The pressure drop generated by the sample has been recorded at three different dry air flow rates (30 l/min, 60 l/min and 90 l/min) as reported by ISO 9360-1 and 9360-2, specific for these HME devices. The resistance along the device is measured by an electronic differential pressure gauge (2080P, Digitron, United Kingdom); in all measurements, the pressure drop due to the instrument is calculated and subtracted from the sample pressure drop.

Sample Moisture Absorption Ability (ΔHrec)

To evaluate the moisture absorption ability of the sample, an apparatus has been used capable to simulate the patient's breathing, which allowed to perform alternate flow tests in compliance with the European Standard ISO 9360:1 "Anaesthetic and Respiratory Equipment—Heat and Moisture Exchangers (HMEs) for Humidifying Respective Gases in Humans—Part 1: HMEs for Use with Minimal Tidal Volumes of 250 mL".

This technique, of the gravimetric type, is suitable for evaluating the performance of the HME device. ISO 9360 defines the following experimental conditions: the ratio between inspiration and expiration time is 1:1; the current volume is 500 mL; 15 breaths per minute and a flow rate of 7.5 l/min. Besides, the water temperature inside the humidifier must be set at 37.5° C. (maximum value allowed by ISO).

The humidity % absorbed by the device ($\Delta H_{rec}$%) is calculated by the following formulas:

$$\text{Moisture output} = \Delta H_{exp} - \text{moisture loss}$$

$$\Delta H_{rec}(\%) = \frac{\text{Moisture output}}{\Delta H_{exp}} \times 100$$

wherein $\Delta H_{exp}$ is the humidity contained in the air entering the device, "moisture output" is the humidity absorbed by the device and "moisture loss" the humidity contained in the air leaving the device.

Example 1

This example refers to the synthesis procedure of HME devices based on gelatin and chitosan chemically cross-linked with genipin.

Reactants:

Quantities for obtaining 8 cylindrical gelatin-chitosan filters 35 mm in height and 50 mm in diameter:

gelatin solution: 10 g of gelatin (Italgelatine—bloom: 280, mesh: 4) dissolved in 391.4 mL of water under constant magnetic stirring at 40° C. for 1 h.

chitosan solution: 5 g of chitosan (Sigma Aldrich, low molecular weight) dispersed in 334.9 g of water under vigorous stirring; when the dispersion was homogeneous, 3.4 g of acetic acid (Sigma Aldrich, purity ≥99%) were added to achieve complete dissolution by magnetic stirring and ultrasound (1 h).

genipin solution: 0.3 g of genipin (Wako chemicals) were dissolved in 30 g of water in an ultrasonic bath (30 min).

Procedure:

290 mL of the chitosan solution were poured into the gelatin solution at room temperature and a slow magnetic stirring was maintained to avoid foaming until the system was completely homogenized (15 min). The gelatin:chitosan weight ratio obtained was equal to 70:30, and the quantity of gelatin and chitosan used was such that the concentration of the polymer part in the hydrogel obtained at the end of step f) was 2% by weight.

28.6 mL of the genipin solution were added to the mixture obtained in the previous step, and magnetic stirring was maintained for 15 min; genipin was used in amounts equal to 2% by weight with respect to the sum of gelatin and chitosan weights.

The solution obtained was poured into cylindrical molds with an internal diameter of 50 mm, consisting of a 1 mm thick steel bottom and 1.5 mm thick PVC walls, until obtaining a solution level height in the mold of 35 mm; the molds were then closed by covering them with plastic lids, taking care not to touch the solution with the lid, and the solution was left to stand for 64 h, time necessary for cross-linking.

The lids of the molds were then removed before the freeze-drying, performed by setting the following parameters:

Freezing temperature=−40° C.;
First drying ramp=5° C./h up to −5° C.;
Second drying ramp=1° C./h up to 15° C.

For the realization of the cooling and heating phases, the thermally conductive bottom of the container was placed in contact with a surface initially at room temperature. During these phases, the temperature was controlled with a thermocouple inserted into the sample at the center of its upper surface; the probe is connected through a feedback system to a logic circuit that controls a temperature programmer, in turn in contact with the surface on which the container is placed.

At the end of the freeze-drying, 5 mm of sample from above and 3 mm from below were mechanically removed (the terms "high" and "low" refer to the orientation of the samples in the containers during step e).

Example 2

This example refers to the synthesis procedure of HME devices based on gelatin and chitosan cross-linked by dehydrotermal treatment (DHT).

The gelatin and chitosan solutions were prepared as described in Example 1, with the difference that after mixing the two solutions the crosslinker solution was not added, but only 28.6 g of water; the gelatin and chitosan solutions were used in quantities and ratios identical to those of Example 1.

Procedure:

The chitosan solution was poured into the gelatin solution at room temperature and the resulting solution was kept under slow magnetic stirring to avoid foaming until complete homogenization of the system (30 min).

The obtained solution was poured into the molds and left to rest until hydrogel achievement, after about 3 hours as visually verified (step d).

The freeze-drying (step e) was carried out following the same thermal profile of Example 1. On the samples so freeze-dried, the DHT cross-linking step (step f) was carried out, inserting them in a stove and setting a vacuum degree of P=0.001 mbar and a temperature of 160° C. The samples were maintained under these conditions for 48 h, conditions necessary for crosslinking to take place.

At the end of cross-linking, 5 mm of sample from above and 3 mm from the bottom were mechanically removed.

Example 3

This example refers to the synthesis procedure of a HME device based on gelatin and chitosan chemically crosslinked with genipin following the procedure of Example 1 and varying the gelatin:chitosan ratio which, in this case, is equal to 50:50. Example 1 was repeated by changing only the amounts and concentrations of chitosan and genipin solutions as described below:

chitosan solution: 10 g of chitosan (Sigma Aldrich, low molecular weight) dispersed in 574.2 g of water under vigorous stirring; when the dispersion resulted homogeneous, 5.8 g of acetic acid (Sigma Aldrich, purity 99%) were added to achieve complete dissolution by magnetic stirring and ultrasound (1 h); a volume of chitosan solution equal to 580 mL was obtained;

genipin solution: 0.4 g of genipin (Wako Chemicals) were dissolved in 40 g of water in an ultrasonic bath (30 min), obtaining a total solution volume of 40 mL.

Example 4

This example refers to the synthesis procedure of a HME device based on gelatin and chitosan chemically crosslinked with genipin following the procedure of Example 1 and varying the gelatin:chitosan ratio which, in this case, is equal to 80:20. Example 1 was repeated by changing only the amounts and concentrations of chitosan and genipin solutions as described below:

chitosan solution: 2.5 g of chitosan (Sigma Aldrich, low molecular weight) dispersed in 207.9 g of water under vigorous stirring; when the dispersion resulted homogeneous, 2.1 g of acetic acid (Sigma Aldrich, purity 99%) were added for achieving complete dissolution by magnetic stirring and ultrasound (1 h); total volume of chitosan solution 210 mL;

genipin solution: 0.25 g of genipin (Wako Chemicals) were dissolved in 25 g of water in an ultrasonic bath (30 min), obtaining a total volume of genipin solution equal to 25 mL.

Example 5

This example refers to the synthesis procedure of a HME device based on gelatin and chitosan chemically crosslinked with genipin following the procedure of Example 1 and varying the polymer part concentration in the hydrogel obtained at the end of step d'), that, in this case, is equal to 3% by weight. Example 1 was repeated only changing the concentrations of gelatin and chitosan solutions as described below:

10 g of gelatine (Italgelatine—bloom: 280, mesh: 4) were dissolved in 196.4 mL of water under constant magnetic stirring at 40° C. for 1 h, obtaining a volume of gelatin solution equal to 196.4 mL;

4.29 g of chitosan (Sigma Aldrich, low molecular weight) were dispersed in 257.4 g of water under vigorous stirring; when the dispersion resulted homogeneous, 2.6 g of acetic acid (Sigma Aldrich, purity 99%) were added for achieving complete dissolution by magnetic stirring and ultrasound (1 h); 260 mL of chitosan solution were obtained.

Example 6

This example refers to the synthesis procedure of a HME device based on gelatin and chitosan chemically crosslinked with genipin following the procedure of Example 1 and varying the concentration of genipin, which, in this case, is equal to 1% by weight with respect to the sum of gelatin and chitosan weights. Example 1 was repeated only changing the concentration of the genipin solution as described below:

genipin solution: 0.143 g of genipin (Wako Chemicals) were dissolved in 28.6 g of water in an ultrasound bath (30 min), obtaining a total solution volume of 28.6 mL.

Example 7

This example refers to the synthesis procedure of a HME device based on gelatin and chitosan chemically crosslinked with genipin following the procedure of Example 1 and varying only the concentration of the genipin, which, in this case, is equal to 4% by weight with respect to the sum of the gelatin and chitosan weights. Example 1 was repeated only changing the concentration of the genipin solution as described below:

genipin solution: 0.571 g of genipin (Wako Chemicals) were dissolved in 28.6 g of water in an ultrasound bath (30 min), obtaining a total solution volume of 28.6 mL.

Example 8

This example refers to the synthesis procedure of a HME device based on gelatin and chitosan chemically crosslinked with genipin following the procedure of Example 1 and varying only the concentration of the genipin, which, in this case, is equal to 0.5% by weight compared to the sum of gelatin and chitosan weights. Example 1 was repeated only changing the concentration of the genipin solution as described below:

genipin solution: 0.071 g of genipin (Wako chemicals) were dissolved in 28.6 g of water in an ultrasound bath (30 min), obtaining a total solution volume of 28.6 mL.

Example 9

This example refers to the synthesis procedure of an HME device based on gelatin and chitosan cross-linked by dehydrotermal treatment (DHT) following the procedure of Example 2 with the only difference that in this case the procedure was not carried out under vacuum but at atmospheric pressure.

The gelatin and chitosan solutions were prepared as described in Example 2 and were employed in amounts and ratios identical to those of Example 2.

Example 10

This example refers to the synthesis procedure of an HME device based on gelatin and chitosan cross-linked by dehydrotermal treatment (DHT) following the procedure of Example 2 with the only difference that the crosslinking time, in this case, was equal to 24 hours.

The gelatin and chitosan solutions were prepared as described in Example 2 and were employed in amounts and ratios identical to those of Example 2.

Example 11

A sample prepared as described in Example 1 was subjected to a pressure drop test according to standards ISO 9360-1 and ISO 9360-2. The results are shown in FIG. 3, where it can be seen that the sample complies with the parameters defined by the reference standards, that is, a pressure drop not greater than 5 mbar. Similar results were obtained with the samples prepared in Examples 3 and 7, as confirmed by the values shown in FIG. 3.

Example 12

A sample prepared as described in Example 2 were subjected to a test to evaluate the ability to absorb water (also called swelling). The results are shown in FIG. 4, where it can be seen that the sample has a high capacity to absorb water due to its high hydrophilicity, a fundamental property for this type of devices that must be able to quickly absorb the moisture present in the flow of expired air and release it to the flow of inspired air.

Similar results were obtained with the samples prepared in Examples 9 and 10, as confirmed by the values shown in FIG. 4.

Example 13

A sample prepared as described in Example 1 was subjected to a moisture absorption capacity test according to standards ISO 9360-1 and 9360-2. The result is shown in FIG. 5, in which it is observed that the parameters defined by the reference standards, that is, an absolute humidity recovery of about 80%, are respected. Similar results were obtained with the samples prepared in Examples 3 to 6 as confirmed by the values shown in FIG. 5.

Example 14

This example refers to the synthesis procedure of HME devices composed of a core based on sodium alginate on the fibers of which HA modified with $Fe^{2+}$ and $Fe^{3+}$ is biomineralized, and a shell based on gelatin and chitosan chemically crosslinked with genipin following the procedure of Example 1.

Synthesis of the Paramagnetic Core
Reactants:
1) Acid water solution: 4.44 g of phosphoric acid ($H_3PO_4$, purity=85%; Sigma-Aldrich) dissolved in 30 mL of water.
2) Basic dispersion: 5 g of calcium hydroxide ($Ca(OH)_2$, purity=95%; Sigma-Aldrich) dispersed in 40 mL of water at 50° C. under mechanical stirring.
3) $Fe^{2+}$ solution: 2.58 g of ferrous chloride ($FeCl_2 \times 4H_2O$, purity>99%; Sigma-Aldrich) dissolved in 15 mL of water.
4) $Fe^{2+}$ solution: 3.5 g of ferric chloride ($FeCl_3 \times 6\ H_2O$, purity>99%; Sigma-Aldrich) dissolved in 15 mL of water.
5) Alginate solution (5% by weight): 5 g of Alginate (Sigma-Aldrich) dissolved in 95 mL of water.
6) 1 M calcium chloride solution: 55.49 g of calcium chloride ($CaCl_2$), Sigma-Aldrich) dissolved in 500 mL of water.

Method:
To the solution of calcium hydroxide placed under mechanical stirring at 50° C., the two solutions containing iron ions were added simultaneously and quickly; subsequently the acid solution was added dropwise within the reagent mixture, and subsequently to the mixture 85 mL of alginate solution were added dropwise. Once the dripping was over, the mixture was left to stand for 2 hours to allow the growth of modified hydroxyapatite crystals, in which the iron ions are present with a Fe:Ca ratio equal to 40 mol %; at the end, the product was centrifuged and washed three times with distilled water. The so obtained compound, containing a quantity of water equal to 99% by weight, was inserted into metal molds with a diameter equal to 2 mm and freeze-dried by setting the following parameters:

Freezing temperature=−40° C.;
First drying ramp=5° C./h up to −5° C.;
Second drying ramp=1° C./h up to 15° C.

At the end of the freeze-drying, without removing the sample from the mold, a 1 M $CaCl_2$) solution was introduced into the mold to reticulate/stabilize the sample; the crosslinking took place in 3 hours and subsequently the sample, which after the treatment assumed a more consistent appearance, was washed three times with distilled water.

Synthesis of the Polymeric Shell
The gelatin, chitosan and genipin solutions were prepared as described in Example 1 and were employed in amounts and ratios identical to those of Example 1.

Method:
The chitosan solution was poured into the gelatin solution at room temperature and the resulting solution was kept under slow magnetic stirring to avoid foaming until complete homogenization of the system (30 min).

The genipin solution was added to the mixture obtained in the previous step, and magnetic stirring was maintained for 15 min.

The obtained solution was poured into molds having an internal diameter of 50 mm, equal to those used in Example 1, until obtaining a height of the level of the solution in the mold equal to 35 mm; within and at the center of the same molds before the solution the superparamagnetic core synthesized as described above in point a) were introduced; the molds were then closed by covering them with plastic lids, taking care not to touch the solution with the lid, and the solution was left to stand for 64 h, a time necessary for cross-linking.

The lids of the molds were then removed before the freeze-drying, carried out following the same thermal profile of Example 1.

At the end of the freeze-drying, 5 mm of sample from the top and 3 mm from the bottom were mechanically removed.

Example 15

This example refers to the synthesis procedure of HME devices consisting of a core based on sodium alginate mixed with HA modified with $Fe^{2+}$ and $Fe^{3+}$ (FeHA) and a shell based on gelatin and chitosan chemically crosslinked with genipin following the procedure of Example 1.

Synthesis of the Paramagnetic Core

Reactants:
7) Acid water solution: 44.40 g of phosphoric acid ($H_3PO_4$, purity=85%; Sigma-Aldrich) dissolved in 300 mL of water.
8) Basic dispersion: 50 g of calcium hydroxide ($Ca(OH)_2$, purity=95%; Sigma-Aldrich) dispersed in 400 mL of water at 50° C. under mechanical stirring.
9) $Fe^{2+}$ solution: 25.80 g of ferrous chloride ($FeCl_2 \times 4H_2O$, purity>99%; Sigma-Aldrich) dissolved in 150 mL of water.
10) $Fe^{3+}$ solution: 35 g of ferric chloride ($FeCl_3 \times 6 H_2O$, purity>99%; Sigma-Aldrich) dissolved in 150 mL of water.
11) Alginate solution (10% by weight): 16.20 g of Alginate (Sigma-Aldrich) dissolved in 145.8 mL of water.
12) Calcium chloride solution 1M: 55.49 g of calcium chloride ($CaCl_2$), Sigma-Aldrich) dissolved in 500 mL of water.

Method:

To the solution of calcium hydroxide placed under mechanical stirring at 50° C., the two solutions containing iron ions were added simultaneously and quickly; subsequently the acid solution was dripped into the reaction, which continued for two hours in temperature and under stirring, then was left for 24 hours at rest to allow the growth of the modified hydroxyapatite crystals, where the iron ions are present with a Fe:Ca ratio equal to 40 mol %; at the end, the product (FeHA) was centrifuged, washed three times with distilled water and dispersed in distilled water reaching a total volume of 200 mL. To the alginate solution 10% by weight the FeHA suspension was added at room temperature and through an ultrasonic bath so as to obtain an alginate: FeHA ratio equal to 20:80. The mixture was subsequently poured into metal molds with a diameter of 2 mm and freeze-dried by setting the following parameters:

Freezing temperature=–40° C.;
First drying ramp=5° C./h until –5° C.;
Second drying ramp=1° C./h until 15° C.

At the end of the freeze-drying, without removing the sample from the mold, a 1 M $CaCl_2$) solution was introduced into the mold to reticulate/stabilize the sample; the cross-linking took place in 3 hours and subsequently the sample, which after the treatment assumed a more consistent appearance, was washed three times with distilled water.

Synthesis of the Polymeric Shell

The gelatin, chitosan and genipin solutions were prepared as described in Example 1 and were employed in amounts and ratios identical to those of Example 1.

Method:

The chitosan solution was poured into the gelatin solution at room temperature and the resulting solution was kept under slow magnetic stirring to avoid foaming until complete homogenization of the system (30 min).

The genipin solution was added to the mixture obtained in the previous step, and magnetic stirring was maintained for 15 min.

The obtained solution was poured into molds having an inner diameter of 50 mm, equal to those used in Example 1, until a solution level height of 35 mm was obtained in the mold. Within and at the center of the same molds before the solution, the superparamagnetic core synthesized as described above at point a) were introduced; the molds were then closed by covering them with plastic lids, taking care not to touch the solution with the lid, and the solution was left to stand for 64 h, a time necessary for crosslinking.

The lids of the molds were then removed before the freeze-drying, carried out following the same thermal profile of Example 1.

At the end of the freeze-drying, 5 mm of sample from the top and 3 mm from the bottom were mechanically removed.

The invention claimed is:
1. Process for preparing a material useful for the production of Heat and Moisture Exchange (HME) filters, which comprises the following steps:
   a) preparing an acidic aqueous solution of chitosan in a concentration from 1 to 2.5% by weight;
   b) preparing an aqueous solution of a gelatin of animal origin in a concentration from 2.5 to 5% by weight, operating at a temperature between 40 and 50° C.;
   c) mixing the two solutions from steps a) and b) in such quantities as to obtain a mixture having a weight ratio of gelatin:chitosan from 80:20 to 50:50, gently stirring the mixture to avoid the formation of a foam until obtaining a homogeneous solution, and subsequently diluting the homogeneous solution to obtain a polymer solution having a total polymer concentration of from 2 to 4% by weight;
   d) pouring the polymer solution prepared in step c) into a container with the bottom made of a material having thermal conductivity greater than or equal to 15 W/(m·K) and side walls made of a material having thermal conductivity less than or equal to 1 W/(m·K);
   e) freeze-drying, inside said container, the polymer solution obtained in step c) according to the following phases:
      freezing the polymer solution to a temperature of from –20 to –60° C. by placing the bottom of the container in contact with a refrigerating system;
      primary drying by heating with a rate between 2 and 8° C./h up to a temperature between –5 and –10° C., operating at a pressure between 0.001 mbar and atmospheric pressure and;
      secondary drying by heating with a rate between 1 and 5° C./h up to a temperature between 15 and 20° C., operating at a pressure between 0.001 mbar and atmospheric pressure; and
   f) a crosslinking treatment consisting of a step of subjecting the freeze-dried product obtained in step e) to a thermal dehydration.

2. The process according to claim 1, wherein the container has the bottom made with steel, copper or silicon, and the walls made with a plastic, teflon or glass.

3. The process according to claim 1, wherein step f) is carried out with a heat treatment which consists in subjecting the freeze-dried product obtained in step e) to a temperature from 140 to 160° C. at a pressure between 0.001 mbar and the atmospheric pressure and for a duration between 24 and 48 h.

4. The process according to claim 1, wherein, prior to the pouring of the polymer solution in step d) to serve as a surrounding polymeric material, the same container is introduced a paramagnetic core comprising a hydroxyapatite in which an amount of between 2 and 40 atomic % of calcium is replaced by iron present in both oxidation states (II) and (III), produced by a process which comprises the following steps:

- g) preparing an aqueous solution containing a precursor of calcium, at least one soluble salt of iron (II) and at least one soluble salt of iron (III);
- h) preparing an aqueous solution containing a water soluble compound of phosphorus;
- i) preparing an aqueous solution containing a precursor of one or more hydrophilic polymers;
- j) slowly adding the phosphorus compound solution to the solution containing the precursor of calcium and the iron salts, obtaining a suspension;
- k) optionally, immediately adding the solution obtained in step i) to the suspension obtained in step j);
- l) If step k) has been carried out, allowing the suspension to react at a temperature between ambient T and 70° C. for a time between 1 and 5 hours;
- k') in case steps k) and l) have not been carried out, allowing the system obtained in step j) to react at a temperature between ambient T and 70° C. for a time between 1 and 24 hours; and
- l') if step k') has been carried out, mixing the suspension obtained with the aqueous solution obtained in step i);
- m) subjecting to a freeze-drying treatment of the solution/suspension product obtained in step l) or in step l');
- n) immersing the freeze-dried product from step m) in a $CaCl_2$ solution at a concentration between 0.5 and 1.5 M for a period between 15 and 45 minutes, followed by washing with immersion in distilled water; and
- o) again subjecting to freeze-drying treatment the material of the $CaCl_2$-treated product from step n).

5. The process according to claim 4, wherein sodium alginate is used as hydrophilic polymer.

6. The process according to claim 4, wherein the weight ratio between the paramagnetic core and the surrounding polymeric material is between 40:60 and 80:20.

7. The process according to claim 1, wherein, at the end of the process, between 3 and 5 mm of the upper face and of the lower face of the obtained product are mechanically removed.

8. The process according to claim 4, wherein the water soluble compound of phosphorus employed in step h) is phosphoric acid.

* * * * *